(12) United States Patent
Frayne

(10) Patent No.: US 8,088,602 B1
(45) Date of Patent: *Jan. 3, 2012

(54) MANIPULATION OF RNA STABILITY AND PROTEIN SYNTHESIS USING THIO-PHOSPHATE

(76) Inventor: Elizabeth Gay Frayne, Diamond Bar, CA (US)

( * ) Notice: Subject to any disclaimer, the term of this patent is extended or adjusted under 35 U.S.C. 154(b) by 805 days.

This patent is subject to a terminal disclaimer.

(21) Appl. No.: 10/679,305

(22) Filed: Oct. 7, 2003

Related U.S. Application Data

(63) Continuation-in-part of application No. 10/007,489, filed on Dec. 5, 2001, now Pat. No. 7,125,982.

(51) Int. Cl.
*C12P 19/34* (2006.01)
*C07H 21/02* (2006.01)

(52) U.S. Cl. ...................... 435/91.1; 536/23.1

(58) Field of Classification Search ............. None
See application file for complete search history.

(56) References Cited

U.S. PATENT DOCUMENTS

| | | | |
|---|---|---|---|
| 4,703,004 | A | 10/1987 | Hopp et al. |
| 4,782,137 | A | 11/1988 | Hopp et al. |
| 6,528,641 | B2 | 3/2003 | Lader |
| 7,125,982 | B1 * | 10/2006 | Frayne ............... 536/25.33 |

OTHER PUBLICATIONS

Sun et al., J. Biol. Chem. 257 (3): 1347-1353, 1982.*
Chang et al., Anal. Biochem., 188 (2): 300-304, 1990.*
Kamdar et al., Biotechniques 12(5): 632-638, 1992.*
Matzura, H. of Eckstein "A Polyribonucleotide Containing Alternating P=O and P=S Linkases" Eur. J. Biochem. 3 (1968) 448-452.
Bouvet, P. and Belasco J. G. Control of RNase E mediated RNA degradation by 5" terminal base pairing in *E. Coli* Nature (1992) 360:488-491.
Wang Y. et al (2002) Precision and functional specificity in mRNA decay. RNAS 99:5860-5865.
Griffiths, A.D. et al (1987) Steriospecificity of Nucleases towards phosphoratiate substituted RNA: Stereochemistry of transcription by T7 RNA polymerase.
Suh et a (1992) "A phosphorotrioate at the 3" splice-site inhibits the second splicing step in a group lintron" NAR 20: 6303-6309.

* cited by examiner

*Primary Examiner* — Nancy Vogel

(57) ABSTRACT

The present invention describes the use of thio-phosphate as a novel metabolite for chemically modifying mRNA in cells. Thio-phosphate is taken up by both prokaryotic and eukaryotic cells, incorporated into rNTP pools and ultimately mRNA. This enables the in vivo modification of mRNA with nuclease resistant phosphorothioate internucleotide linkages. Significant incorporation of thio-phosphate occurs such that RNA is significantly stabilized from degradation both in vivo and in vitro upon subsequent isolation. Thio-phosphate can be used as the sole source of phosphate in the culture medium for several generations resulting in a significant increase in the amount of mRNA per cell. The method should facilitate the detection and analysis of mRNA for research and diagnostic purposes. To enhance protein production it is necessary to use a mixture of thio-phosphate and phosphate in the culture medium. Generally a specific ratio of thio-phosphate to phosphate results in the optimal synthesis of many proteins for a given organism. Significant increases in both native and recombinant proteins are possible with the use of thio-phosphate in the culture media. The method represents a significant advance for cell culture with the potential to not only enhance a variety of fermentation reactions but to also potentially stimulate cellular differentiation for a variety of therapeutic purposes.

1 Claim, 3 Drawing Sheets

TABLE 1

| GENE | ORGANISM | ASSAY | RELATIVE ACTIVITY RATIO | | | | | |
|---|---|---|---|---|---|---|---|---|
| | | | 100 | 70 | 50 | 30 | 10 | 0 |
| Alkaline phosphatase | E. coli: plasmid | Enzyme Activity | → | – | ↑ 3-5 | ↑ | – | – |
| Beta-galactosidase | E. coli: plasmid | Enzyme Activity | → | – | → | → | → | – |
| Alkaline phosphatase | S. cerevisiae: YEP plasmid | Immune ppt | ↑ | ↑ | ↑ | ↑ | ↑ 10X | – |
| Actin | S. cerevisiae | mRNA | ↑ 10X | NT | ND | NT | NT | ND |
| Extracellular nuclease | S. cerevisiae | Enzyme Activity | → | → | → | – | ↑ 2-3X | – |
| Lipase | P. canadensis | Enzyme Activity | → | → | → | → | ↑? (<2X) | – |

ND (Not Detected); – (Normal Control Level); NT (Not Tested)

MANIPULATION OF RNA STABILITY AND PROTEIN SYNTHESIS USING THIO-PHOSPHATE

BACKGROUND OF THE INVENTION

1. Field of the Invention

The present invention is a continuation-in-part of application Ser. No. 10/007,489, Filed Dec. 5, 2001, incorporated by reference and now U.S. Pat. No. 7,125,982 and related application Ser. No. 10/760,156 (pending) and continued-in-part herein. Thio-phosphate can be used as a feed source substituting for phosphate to chemically modify nucleic acids in vivo. Cells incubated in thio-phosphate containing media incorporate the modified phosphate into the backbone of RNA resulting in RNA modified with nuclease resistant phosphorothioate linkages. The extent of thio-phosphate substitution can be varied by varying the ratio of thio-phosphate to phosphate in the culture media. Cells grown in fully substituted thio-phosphate media generate higher yields of mRNA per cell. The consequences for cells are both profound and subtle allowing for continued growth and viability over several generations.

Reduced ratios of thio-phosphate to phosphate are used to maximize protein synthesis. Both native and recombinant protein synthesis can be significantly enhanced. The optimal ratio of thio-phosphate to phosphate for enhancing protein synthesis varies with the organism as well as the physiological state of the cell. The novel mRNA stabilizing media can be used to increase the protein levels of native and/or recombinant proteins in prokaryotes as well as eukaryotes.

2. Description of Related Disclosures

Phosphorothioate linkages in RNA are known to protect such molecules from degradation by RNases found in serum or inside cells (Matzura and Eckstein (1968) European J. Biochem. 3:448-452). The in vivo incorporation of thio-phosphate into the mRNA backbone provides a ready means to induce the stabilization of cellular mRNAs. Bacterial mRNAs are very unstable with half-lives on the order of ~5 minutes (Bouvet and Belasco (1992) 360:488-491). Eukaryotic mRNAs are considerably more stable with half-lives that range from 20 minutes to 10 hours or more (Wang, Y. (2002) PNAS 99:5860-5865).

Most methods for increasing the yield of mRNA focus on improved extraction methods that stabilize mRNA in vitro via RNase inhibitors (Lader (2003) U.S. Pat. No. 6,528,641). The present method is quite distinct allowing for both in vivo and in vitro stabilization of mRNA by chemical modification of mRNA. In vivo stabilization of bulk mRNA should be useful for detecting rarer messages, unstable messages, processing intermediates, as well as reducing the quantity of material needed for screening samples for particular mRNAs. Note, the use of fully substituted media does not necessarily preserve the natural state of the cell making it more useful for obtaining qualitative and structural information.

Thio-phosphate can also be used to enhance the protein synthesis of many genes. An advantage of this method is that the compound can be used to induce gene expression. In fact, it is often possible to simply add the modified phosphate to the media or feed source since only a fraction of the total phosphate needs to be modified for enhanced protein expression Thio-phosphate is utilized by a variety of organisms and cell types making it readily adaptable for different applications. Enhanced protein synthesis via thio-phosphate is not restricted by choice of vector or promoter and increases in both recombinant and non-recombinant proteins are obtained. The level of enhancement can be as much as ten fold.

An additional advantage of using chemical modification via thio-phosphate is that many genes can be induced simultaneously resulting in a balanced and coordinated induction of enzymes or proteins. This aspect may be particularly important for eukaryotic cells as protein folding can be a complex event requiring many accessory proteins (Hartl and Hayer-Hartl (2002) Science 295:1852-1858). Modifying proteins important for glycosylation etc. may also be enhanced (Dwek et al (2002) Nature Reviews 1:65-75). Coordinating multiple reaction steps through the increased synthesis of rate limiting enzymes or proteins may also be important for bio-catalytic reactions. For large scale fermentation reactions it is also an advantage that the enhancement is a non-mutable or irreversible event.

Methods to maximize the synthesis of proteins vary and include vectors with strong viral or cellular promoters, gene amplification (Yeung et al (1983) J. Biol. Chem. 258:15179-15185), and viral expression vectors (Kaufman (1990) Methods in Enzymology Vol. 185:155-198). Some attempts have been made to increase the stability of recombinant gene products using stabilizer elements. Hairpins to block the decay of mRNA are often time consuming to generate and not predictable with a real possibility of impairing translation (Arnold et al (1998) RNA 4:319-330; Emory et al (1985) Genes Dev. 6; 135-148). Genetic mutants such as RNase deficient mutants have also been generated. RNase mutants are lethal and partial mutants or temperature sensitive mutants must be obtained (Jain (2002) Mol. Microbiol. 43:1053-1064). The present method provides a powerful means to increase the stability of mRNA without inhibiting mRNA processing or impairing cellular viability. It is a very effective technology protecting mRNA from multiple degradative pathways.

SUMMARY OF THE INVENTION

The present invention provides a novel approach for manipulating the stability of RNA in vivo. A universal mechanism allows all types of cells to uptake thio-phosphate, after which the modified phosphate enters nucleotide pools. Ultimately the modified phosphate is incorporated into nucleic acids resulting in nuclease resistant phosphorothioate linkages. The approach can be used to facilitate the detection of rarer or unstable mRNAs and/or to increase the total amount of mRNA yield per cell. The in vivo incorporation of thio-phosphate into RNA can also be used to enhance the protein synthesis of genes by increasing the stability of their respective mRNAs. Maximal protein synthesis is achieved by partial substitution of the RNA backbone. Growth in thio-phosphate containing medias allows for the enhancement of both recombinant and native protein synthesis in both prokaryotes and eukaryotes.

BRIEF DESCRIPTION OF THE DRAWINGS

FIG. 2 depicts a table summarizing the results of enhanced protein and mRNA expression with thio-phosphate containing media. Varying ratios of thio-phosphate to normal phosphate were tested for gene specific activity in cultured microorganisms. A 100% ratio represents maximal substitution of the media with thio-phosphate. Arrows pointing upward represent enhanced expression relative to normal media whereas those pointing downward represent diminished expression. Thicker arrows correspond to a greater degree of change than thinner arrows. The approximate fold enhancement is indicated next the to arrow at peak expression.

DESCRIPTION OF THE PREFERRED EMBODIMENTS

The present invention involves a novel approach of labeling cells with a modified metabolite. The most common form of labeling is radioactive labeling. However, during radiolabeling trace amounts of a precursor are used to avoid damage to the cell. It has also been possible to introduce modified amino acids either into the media or by genetically altering cells to make and accept such amino acids (Kowal et al (2001) PNAS 98:2268-2273; Saks, M. E. (2001) PNAS 98:2125-2127). The unusual amino acids are then incorporated into proteins. In general as enzymes are highly specific there is little play in substrate specificity. In fact many substrate analogs are competitive inhibitors. The present invention involves the use of thio-phosphate as a substitute for normal phosphate. This compound is incorporated with a high efficiency such that it can serve to fully replace normal phosphate in the media. The result is the subsequent incorporation of the modified phosphate into dNTP and NTP precursor pools and ultimately nucleic acids. The ability to modify the atom adjacent to phosphate may be significant for in vivo NMR imaging; particularly since $^{31}P$ has such a high natural abundance and high magnetic moment (Lesney, M. S. (2003) Modern Drug Discovery 6:37-39). It might be possible to detect growing cells, dead cells, and/or resting cells using thio-phosphate as an imaging reagent.

Figure 1:
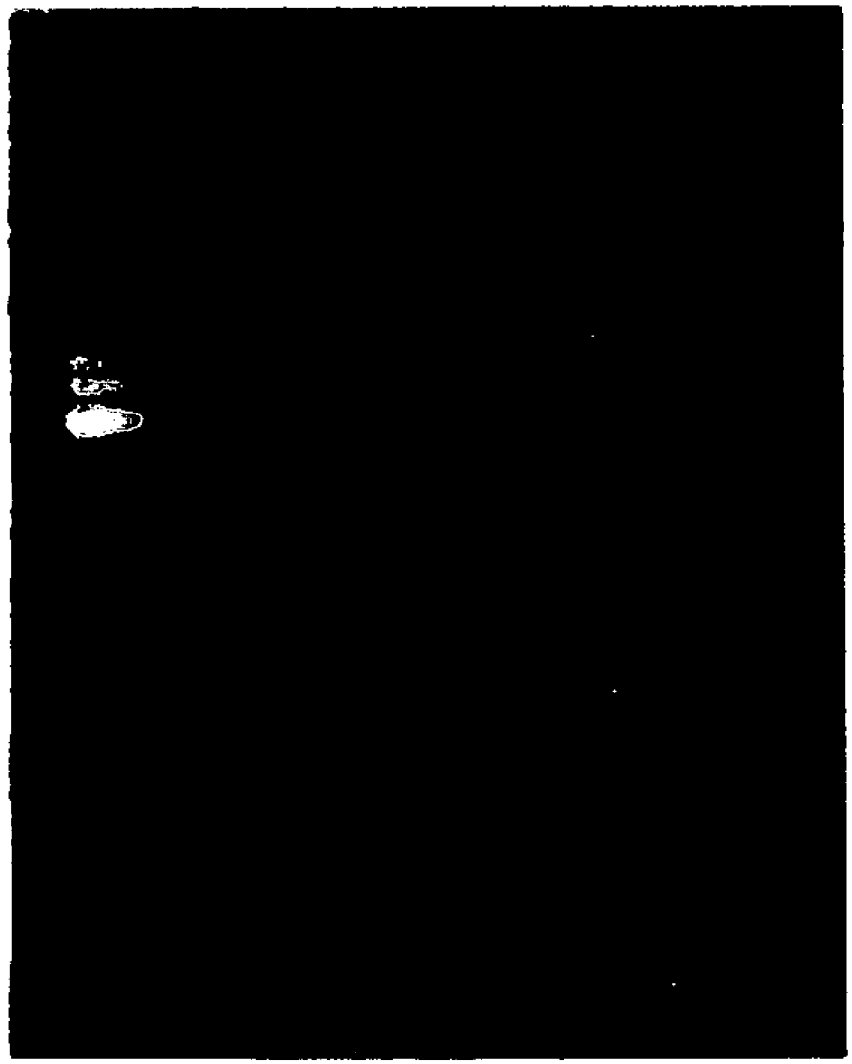
FIG. 1 demonstrates the stabilization and normal RNA processing of yeast actin mRNA in cells grown in thio-phosphate containing media. Total RNA was isolated from cells grown in media with varying ratios of thio-phosphate to normal phosphate and used for Northern analysis. Marker corresponds to biotinylated QX174/Hinf digest (151-726 bp). Lanes 1-4 correspond to RNA from cells grown at ratios of 100%, 50%, 20%, and 0% thio-phosphate to phosphate respectively. Arrow indicates band of the expected MW for mature mRNA with intron removed visible in lane 1 using ~0.5-1 ug of total RNA from 100% substituted media. Trace amounts of a larger processing intermediate can also be discerned (lane 1).

Media substituted with 100% thio-phosphate can be used to increase the mRNA content per cell and thereby facilitate northern, RT-PCR, or other subsequent analyses. While full-strength medias provide the maximum stabilization of mRNA it must be kept in mind that at such levels RNA processing or regulatory mechanisms may be impaired (Suh et al (1992) Nucleic Acids Research 20:6303-6309). In this regard, since both bacteria, yeast, and fish intestinal cells grow readily in 100% thio-phosphate substituted media such processing if impaired must not be necessary for viability (Frayne, Ser. No. 10/007,489 filed Dec. 5, 2001). Furthermore, yeast cells grown in 100% thio-phosphate substituted media and are able to splice introns for such genes as actin (FIG. 1).

Enhanced expression and yields of mRNA per cell may be quite useful for diagnostic applications. In particular, increased mRNA levels may be beneficial for human genetic tests where nonsense mediated decay of mutant genes and/or low level expression limits their detection in lymphocytes by RTPCR. In addition, it should be possible to culture pathogenic micro-organisms in the presence of thio-phosphate and look at gene specific markers of interest to assist in detecting and/or classifying the disease state. Furthermore, the ability to stimulate mRNA production may be useful for inducing cell differentiation in culture which may aide in the creation of artificial organ systems for the liver as well as other cultured products. In this regard it is not inconceivable that the compound could have therapeutic benefits for humans as well.

Thio-phosphate can also be used to increase the protein synthesis of many mRNAs. Generally an optimal ratio of thio-phosphate to phosphate must be found. Very high ratios of thio-phosphate to phosphate will result in a decrease in total protein synthesis. Optimal protein synthesis occurs at lower ratios where total cellular protein levels are not affected but total secreted protein levels may be enhanced. The ratio of thio-phosphate to phosphate rather than the total thio-phosphate level is important for conferring the degree of stabilization. The degree of enhancement may depend somewhat on the natural stability of the mRNA. Less stable and heterologous gene products may be enhanced preferentially. In yeast it is known that many mRNAs for extracellular hydrolytic enzymes such as amylase are atypically stable with half-lives more than ten hrs. In contrast, most yeast mRNAs have half-lives on the order of 20 mins. Very low ratios of thio-phosphate to phosphate (10%) in yeast appear to preferentially enhance the accumulation of the more typical mRNAs relative to the abundant and stable hydrolytic mRNA population. The degree of protein enhancement depends somewhat on the relative stability of corresponding mRNAs and can be as much as ten fold for less stable or heterologous gene products in bacteria and/or yeast. Note however, that the coordinated enhancement of many genes may increase the efficiency of specific processes in protein production such as the secretion of proteins above and beyond what is achieved through mRNA stabilization alone.

Enhanced protein synthesis should benefit fermentation reactions used to generate proteins and enzymes as well as bio-catalytic reactions in which microorganisms are used to enzymatically catalyze the synthesis of a variety of chemicals such as organic acids, antibiotics, vitamins, amino acids, polyketides, etc. The degree of enhancement can be controlled by varying the ratio of thio-phosphate to phosphate used and/or by varying the time point of the addition of the modified phosphate to the fermentation reaction. The optimal ratio of thio-phosphate to normal phosphate that enhances protein synthesis of a given gene product must be determined for a given organism. The optimal ratio may also vary under different cellular physiological states such as that imparted by the vector system employed (i.e. plasmid or phage) or growth phase (trophophase versus idiophase). While a generally optimal ratio for most genes may emerge for a given organism it is still possible that an unusually unstable mRNA may be preferentially induced at lower ratios of thio-phosphate to phosphate levels. If the organism can tolerate an increase in total cellular protein than even stable mRNAs may be enhanced over time.

For bio-catalytic reactions there are several ways in which increased mRNA stability could be used to increase production. (It should be remembered that while increased mRNA levels generally result in increased protein levels of a given gene, this is not always the case.) For any given process productivity may be increased by overcoming the rate limiting step(s) in the bio-reaction sequence. If the product is synthesized during the growth or the trophic phase then there are a number of possible points which may be rate limiting such as glucose uptake, glycolysis (often very fast), Kreb's cycle, enzymatic catalysis or product feedback inhibition.

Thus the rate of fermentation, duration, and/or yield of product may be increased depending on which step is rate limiting. If the product is produced during the idiophase as a secondary metabolite then mRNA stabilization of catalytic enzymes involved in the synthesis of the metabolite may also enhance yields during this later stage of fermentation. It is important to keep in mind that the synthesis of many secondary metabolites is regulated by phosphate. This does not pose a problem since it is the ratio and not the level of modified phosphate that is important for stabilization. Furthermore, the modified phosphate may not impart phosphate regulation and as such act as a phosphate deregulated mutant (Martin (1977) Adv. Biochem. Eng. 6:105-127).

Use of thio-phosphate as described here is not limited to traditional culture systems. Many products are obtained from multi-cellular organisms and plants as well as transgeneic versions of these. Modified feed, injection, or submersion of aquatic species in conditioned media (Frayne, Ser. No. 10/007,489 filed Dec. 5, 2001) can be envisioned as meets all environmental, health, and humane treatment regulations.

EXPERIMENTAL

Example I

Method to Increase mRNA Levels in Cells

To maximize mRNA levels cells are grown in minimal media substituted with 100% thio-phosphate. Bacteria and yeast grow quite well in such media. For *E. coli* minimal media is prepared as follows: ($Na_3SPO_3.XH_2O$) 10-15 g/L and KCL (1.5 g/L) ($NH_4)_2SO_4$, 1 g/L; sodium citrate $2H_2O$, 0.5 g/L; Adjust pH to 7.4 and sterile filter. Then add the following: $MgSO_4.7H_2O$, 0.2 g/L (sterilized separately as a conc. solution); (thiamine HCL, 5 ug/L; glucose, 4 g/L sterilized separately by filtration). Glucose can also be sterilized by autoclaving separately. $FeCl_2$ (500 ug/L) can also be added as needed. Thio-phosphate contains variable amounts of water (10-15 per molecule) not included in molecular weight calculations. It is almost 50% water by weight. Note pH control is important in maximizing thio-phosphate stability. To ensure adequate growth use a high density innoculum and dilute 1 to 50. When adapting to other bacteria determine the sensitivity of the organism to thio-phosphate levels. Optimize for KCL as this often is provided as a salt of normal phosphate. If necessary to improve growth use phosphate depleted nutrient broths (see below) and add thio-phosphate. *S. cerevisiae* (Baker's yeast, Ant #7754) grow in the following essential minimal media with no phosphates (EMM [Contents/L: 3 g phthalic Acid, K+, 5 g $NH_4Cl$, 20 g dextrose, 1.05 g $MgCl_2.6H_2O$, 14.7 mg $CaCl_2.2H_2O$, 1 g KCl, 0.04 g $Na_2SO_4$, 1 mg panthothenic acid, 10 mg nicotinic acid, 10 mg myo-inositol, 1 mg biotin, 0.5 mg boric acid, 0.4 mg $MnSO_4$, 0.4 mg $ZnSO_4.7H_2O$, 0.2 mg $FeCl_2.6H_2O$, 40 ug molybdic, 0.1 mg KI, 40 ug $CuSO_4.5H_2O$, 1 mg citric acid], BIO101) and supplemented with thio-phosphate (1 g/L) as well as each of Example II Method of Enhancing Protein Production The stabilization of RNA by growth in thio-phosphate media can be used to enhance the protein synthesis of many proteins. The optimal level of thio-phosphate to phosphate must be determined as well absolute levels of total phosphate that are tolerable. Growth in all cases is enhanced by using enriched media prepared by depleting inherent phosphate. To deplete phosphate by precipitation, $MgSO_4$ and ammonium hydroxide are added to the media of choice. YPD (1% Bacto-yeast extract, 2% Bacto-peptone, 2% Dextrose) phosphate depleted media is prepared by adding 10 ml of 1 M $MgSO_4$ and 10 ml of concentrated $NH_4OH$ per liter and allowing the ppt. to form by leaving the solution at room temp. for 30 min. The media is then filtered and the pH readjusted to pH 6.5. Using this procedure, the detectable amount of ortho-phosphate remaining is less than ~200 mg/liter. Using phosphate levels at ~1 g/L adequate growth is observed over the full range of ratios (100% to 0%) for both *S. cerevisiae* and *Pichia canadensis*. It is best to innoculate at high densities using, for example a 1:20 dilution. Insufficient innoculum (low density) will result in poor growth.

To test for optimal protein synthesis conditions the following system can be used: a recombinant YEp plasmid containing a secreted bacterial alkaline phosphatase gene (YEp-FLAG-1-BAP, Sigma; U.S. Pat. Nos. 4,703,004, 4,782,137 EP Patent 150126, and JP Patent 1983150) marked with the FLAG™ peptide DYKDDDDK. The BAP gene is under the control of an ADH promoter that is activated when glucose levels are exhausted. Detection of the FLAG epitope in cells is possible using immuno test strips (TagDetect kit (Stratagene). To enhance signal detection using the vector it is best to prepare spheroplasts (Yeast Cell Lysis Kit, Bio 101) before lysing cells with glass beads in phosphate buffered saline. It is possible to overwhelm the test strips with antigen and obliterate signal so various dilutions must be tested to ensure accurate results. When yeast cells (BJ3505 strain, Sigma) transformed with the expression vector are grown overnight in media containing different ratios of thio-phosphate to normal phosphate (100, 90, 80, 70, 60, 50, 40, 30, 20, 10, 0), maximal synthesis occurs at a ~10% ratio (weight equivalent) following cessation of growth. In this regard, the optimal ratio can vary somewhat with different lots of thio-phosphate at high purity (>90% purity) because of variable water content and phosphate contamination. While additional peaks are observed at higher ratios the growth rate is slightly reduced at these higher levels making ~10% the preferred ratio requiring less thio-phosphate. Dilution assays indicate an increase of about ten fold compared to normal media with an equivalent amount of phosphate (FIG. 2).

An additional assay was developed to examine the effects of thio-phosphate media on the synthesis of secreted proteins. Yeast excrete many extracellular hydrolases and the mRNAs for these the following at 50 mg/L adenine, histidine, leucine, lysine, and uracil (Sp, BIO101). Various *S. cerevisiase* strains are able to grow in minimal media containing thio-phosphate: multiploid fleischmann's yeast strain, haploid strain ATTC# 32119, and diploid strain BJ3505 (Sigma). The haploid strain *Pichia canadensis* ATTC# 14355 grew better with a yeast nitrogen based media (YNB, BIO 101) as opposed to EMM. Note that the optimal level of total phosphate for yeast is ~1 g/L which is much less than that for bacteria. Again if necessary to improve growth use nutrient broths depleted of phosphate (see below).

To demonstrate enhanced mRNA levels, yeast RNA was isolated from *S. cerevisiae* grown in EMM with thio-phosphate. Yeast RNA can be isolated by methods involving the lysis of cells in the presence of guanidinium salts (TRIazol, MRC; Kadmar and Evans (1992) BioTechniques 12:632-637). Briefly cells are pelleted and an equal volume of acid washed glass beads (Sigma Chemical) added. To this sample a small amount of Triazol is added to initiate lysis. The sample is pipetted up and down while on ice. The sample is then vortexed for 40 sec and placed on ice before vortexing once again. The volume of TRIazol is then increased such that for each ~100 mg of cells, 1 ml of TRIazol is added. Then 0.2 ml of chloroform is added to separate the aqueous and organic phases. After centrifugation the aqueous layer is ppt with isopropanol.

Northern analysis of actin mRNA indicates that significant stabilization of mRNA occurs in 100% thio-phosphate substituted media. The mRNA is in the size range expected for a mature mRNA in which the intron sequences have been removed (FIG. 1). A larger less prominant molecular weight species is also detected suggesting the accumulation of processing intermediates. The actin probe is prepared by amplification of yeast genomic DNA (act), YFL039C, *Saccharomyces* Genome Database http://genome-www2.standford.edu) with the following PCR primers:

SEQ ID NO. 1: 5' GAGGTTGCTG CTTTGGTTAT TG 3' 22 bp

SEQ ID NO. 2: 5' TTGTGGTGAA CGATAGATGG AC 3' 22 bp

PCR cycling parameters using a BIO-RAD thermal cycler and Taq polymerase are as follows: initial denaturation at 94° C. for 4 min. followed by 33 cycles of denaturation at 94° C. for 30 sec, annealing at 45° C. for 30 sec, elongation at 72° C. for 3 min. followed by a final elongation at 72° C. for 7 min. The 1109 bp fragment which does not contain intron sequences is gel purified before photo-labeling with biotin using psoralen biotin (Schleicher & Schuell). Total RNA (~0.5 ug) is separated on a 2% high resolving agarose gel and transferred to a neutral nylon membrane. The probe is hybridized according to S&S protocols and detected by chemilumescence using polaroid film. Normally 10 ug of total RNA is required to see such species.

proteins are generally much more stable than other mRNAs and present at high levels. Extracellular nucleases are detected by monitoring the degradation of genomic DNA by gel electrophoresis. A two to three fold increase of activity is observed at a 10% ratio. Ratios beyond 30% are not stimulatory and above 70% are slightly inhibitory. In contrast, lipase a much more abundant hydrolase is increased less than two fold by qualitative assays (FIG. 2).

The low ratios of thio-phosphate to phosphate required for protein synthesis enhancement in yeast make it possible to simply add thio-phosphate to nutrient broths for maximum yields of protein. For any given media the level of orthophosphate should be determined (Hanna Phosphate Test Kit; Hanna Instruments). Compare with a standard phosphate solution to determine the equivalent amount of salt. Then add the appropriate amount of thio-phosphate. Decay of thio-phosphate is affected by pH (neutral to slightly basic is optimal) and temperature (−20° C. is optimal). For prolonged incubations it may be best to adjust the pH of the media.

Bacterial expression can be examined using the recombinant vector pFLAG-ATS-BAP (Sigma Chemical; U.S. Pat. Nos. 4,703,004, 4,782,137 EP Patent 150126, and JP Patent 1983150) marked with bacterial alkaline phosphatase and under the control of a tac/lac hybrid promoter induced by IPTG. This control plasmid is expressed in the periplasmic fraction by virtue of the N-terminal OmpA signal at high levels. Enzyme activity is easily visualized using colormetric staining of whole cells. 0.5 ml of cells are pelleted and resuspended in pH 9.5 buffer (0.1 M Tris-HCL, 0.1 M NaCL, 50 mM MgCl2) along with 10 ul of NBT (nitroblue tetrazolium, 50 mg/ml) and 5 ul of BCIP (5-bromo-4-chloro-3-indolylphosphate, 50 mg/ml). After sufficient time (there may be a slight delay in the activity of induced cells) the samples are compared and then centrifuged to compare pellets. Various ratios of modified phosphate to phosphate are examined: 0%, 10%, 15%, 20%, 25%, 30%, 40%, 50%, 60, 70%, 80%, 90% and 100%. Because the protein is already present at high levels further induction results in the formation of inactive inclusion bodies. To determine the optimal ratio a lower level of lactose is used in the media to prevent the formation of inclusion bodies during the analysis (M9 minimal media made with 0.1% rather than 0.5% lactose, total phosphate levels of 10 g/L). The host strain employed is JM109 and no activity is observed in bacterial cells without the pFLAG-ATS-BAP expression vector several hours (4-7) after induction in lactose containing media. At low lactose levels the optimal ratio is identified at a 50% ratio of modified phosphate to phosphate and is elevated over controls several fold (FIG. 2).

A recombinant vector containing the beta-galactosidase gene (Promega's TA vector expressed from an SP6 promoter) can also be examined. Enzyme activity is detected via a colormetric assay. Cells are grown in minimal media made with 2% lactose rather than glucose for optimal induction of beta-galactosidase. After several (~4-5) hrs bacterial cells are removed to assay for enzyme activity. To 0.5 ml of cells add 0.5 ml of 200 mM Tris-HCL, pH 7.5 and 5 ul of 1% SDS (sodium dodecyl sulfate). Then add 10 ul of IPTG (100 mM) and 20 ul of X-gal (50 mg/ml), mix and incubate at 37° C. The enzyme is inhibited at low ratios of thio-phosphate to phosphate (5-30%) and recovers from inhibition at higher ratios (50-70%). In the presence of glucose which represses the enzyme, the activity is much lower but can be enhanced 10 fold by using a 50% ratio of thio-phosphate to phosphate.

An examination of protein synthesis in bacteria and yeast indicates that soluble protein levels are not enhanced at low ratios of thio-phosphate to phosphate (10-30%). At higher ratios a slight decline in growth appears to account for a reduction in total protein synthesis detected. To measure protein synthesis 4 ml of cells are pelleted washed in PBS and resuspended in lysozyme solution for bacteria. Cells are then pelleted again and washed in PBS to remove lysozyme. Cells are then lysed in 400 ul of 1% SDS and 0.2 N NaOH. The extract is then diluted in water to 2 ml and assayed using the biuret reagent (Gornall et al (1949) J. Biol. Chem. 177:751). Yeast are assayed without lysozyme.

Example III

Figure 3:
FIG. 3 demonstrates the resistance of intestinal DNA derived from Carassius auratus maintained in an aquarium with thio-phosphate. Lns 1-4 show wild type DNA and Lns 5-8 resistant DNA treated with DNase for 0, 5, 10, and 15 min respectively.

Thio-Phosphate can be Incorporated into the Nucleic Acids of Multi-Cellular Organisms Thio-phosphate can also be utilized by whole animals and/or complex tissues. *Carassius auratus* incorporates thio-phosphate into the DNA of intestinal cells; these cells are known to turnover in adults. Fish can be maintained in distilled water with NovAqua and AmQuel conditioners (U.S. Pat. No. 4,666,610). Goldfish flakes are also added for food. Normal phosphate levels in the aquarium are less than 1 mg/L (Hanna Phosphate Test Kit; Hanna Instruments). Fish are transferred to 100 ml of conditioned media with up to 250 mg/L of thio-phosphate added. No adverse reactions are seen in fish incubated for to two days. Fresh media is prepared daily. Fish are sacrificed and DNA prepared from intestinal cells using DNAzol™ (Molecular Research Center Ohio). The DNA samples are then tested for resistance to DNase digestion. Samples are incubated in a 50 ul rxn with ~1ug of DNA and 0.5 units of DNase for 0, 5, 10, 15 min. at room temp. DNA from 250 mg/L thio-phosphate media is much more resistant than wildtype DNA or DNA from 25 mg/L thio-phosphate media. Normal DNA and 25 mg/L thio-phosphate treated DNA is digested after 5 min. while 250 mg/L thio-phosphate treated DNA persists beyond 15 min. of digestion (FIG. 3).

What is claimed is:

1. A method for stabilizing and/or accumulating cellular RNA in vivo resulting in an increase in the total amount of cellular mRNA per cell as well as the protection of RNA from degradation during subsequent isolation procedures comprising:
   1) preparing cell culture media depleted of phosphate
   2) adding thiophosphate as the sole source of phosphate to the media
   3) culturing cells in the modified media for a sufficient time such that most mRNAs and/or rRNAs are modified with phosphorothioate linkages.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: genomic DNA (iii) HYPOTHETICAL: no (iv) ANTI-SENSE: no (vi) ORIGINAL SOURCE:
      (A) ORGANISM: Saccharomyces cerevisiae
      (B) STRAIN: YFL039C genomic clone (x) PUBLICATION INFORMATION:
      (A) AUTHORS: Murakami Y.
          Naitou M.
          Hagiwara H.
          Shibata T.
          Ozawa M.
          Sasanuma S.I.
          Sasanuma M.
          Tsuchiya Y.
          Soeda E.
          Yokoyama K.
          Yamazaki M.
          Tashiro H.
          Eki T.
      (B) TITLE: Analysis of the nucleotide sequence of chromosome
          VI from Saccharomyces cerevisiae.
      (C) JOURNAL: Nature Genet.
      (D) VOLUME: 10
      (F) PAGES: 261-268
      (G) DATE:1995
      (K) RELEVANT RESIDUES IN SEQ ID NO: 1: 10-31

(xi) SEQUENCE DESCRIPTION: SEQ ID NO: 1:

GAG GTT GCT GCT TTG GTT ATT G        22

(2) INFORMATION FOR SEQ ID NO: 2:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: genomic DNA (iii) HYPOTHETICAL: no (iv) ANTI-SENSE: yes (vi) ORIGINAL SOURCE:
      (A) ORGANISM: Saccharomyces cerevisiae
      (B) STRAIN: YFL039C genomic clone (x) PUBLICATION INFORMATION:
      (A) AUTHORS: Murakami Y.
          Naitou M.
          Hagiwara H.
          Shibata T.
          Ozawa M.
          Sasanuma S.I.
          Sasanuma M.
          Tsuchiya Y.

```
            Soeda E.
            Yokoyama K.
            Yamazaki M.
            Tashiro H.
            Eki T.
    (B) TITLE: Analysis of the nucleotide sequence of chromosome
        VI from Saccharomyces cerevisiae.
    (C) JOURNAL: Nature Genet.
    (D) VOLUME: 10
    (F) PAGES: 261-268
    (G) DATE:1995
    (K) RELEVANT RESIDUES IN SEQ ID NO: 2: 1097-1118

(xi) SEQUENCE DESCRIPTION: SEQ ID NO: 2:

TT GTG GTG AAC GAT AGA TGG AC                                           22
```